United States Patent

Hirayama

(10) Patent No.: US 9,003,864 B2
(45) Date of Patent: Apr. 14, 2015

(54) METHOD FOR ESTIMATING WEAR RESISTANCE OF TREAD PORTION OF TIRE

(75) Inventor: Michio Hirayama, Kobe (JP)

(73) Assignee: Sumitomo Rubber Industries, Ltd., Kobe (JP)

( * ) Notice: Subject to any disclaimer, the term of this patent is extended or adjusted under 35 U.S.C. 154(b) by 244 days.

(21) Appl. No.: 13/537,213

(22) Filed: Jun. 29, 2012

(65) Prior Publication Data

US 2013/0036790 A1    Feb. 14, 2013

(30) Foreign Application Priority Data

Aug. 9, 2011   (JP) ................. 2011-174176

(51) Int. Cl.
  *G01N 19/02* (2006.01)
  *G01N 3/56* (2006.01)
  *G01M 17/02* (2006.01)

(52) U.S. Cl.
  CPC .............. *G01N 3/56* (2013.01); *G01M 17/022* (2013.01)

(58) Field of Classification Search
  CPC ...... G01M 17/022; G01M 17/02; G01N 3/56; G01N 19/02
  USPC ............................................................. 73/8
  See application file for complete search history.

(56) References Cited

U.S. PATENT DOCUMENTS

| | | | |
|---|---|---|---|
| 4,995,197 A * | 2/1991 | Shieh et al. ..................... 451/28 |
| 6,203,588 B1 * | 3/2001 | Schroder et al. ............... 51/293 |
| 6,412,330 B1 * | 7/2002 | Dicello et al. ...................... 73/7 |
| 2006/0156790 A1 * | 7/2006 | Bocquillon et al. ................ 73/8 |

FOREIGN PATENT DOCUMENTS

| JP | 2005-308447 A | 11/2005 |
|---|---|---|
| JP | 2006-1299 A | 1/2006 |
| JP | 2007-279063 A | 10/2007 |
| JP | 2009-198276 A | 9/2009 |

* cited by examiner

*Primary Examiner* — Hezron E Williams
*Assistant Examiner* — Rodney T Frank
(74) *Attorney, Agent, or Firm* — Birch, Stewart, Kolasch & Birch, LLP

(57) ABSTRACT

A method for estimating wear resistance of a tread portion of a tire comprises: a tire manufacturing step in which the tire to be evaluated is manufactured; a rubber seat sampling step in which an evaluation rubber seat is cut out from the tread portion of the tire to include a part of the tread surface; an abrasion step in which the rubber seat is subjected to abrasion by the use of an indoor wear testing machine; and a wear resistance estimating step in which the wear resistance of the tire is estimated based on a state of the wear of the rubber seat caused in the abrasion step.

4 Claims, 4 Drawing Sheets

METHOD FOR ESTIMATING WEAR RESISTANCE OF TREAD PORTION OF TIRE

BACKGROUND OF THE INVENTION

The present invention relates to a method for estimating wear resistance of the tread portion of a tire capable obtaining estimation results having high correlations with actual wear resistance of the tire when rolling on the road.

Heretofore, a method employed to estimate wear resistance of the tread portion of a tire is such that a vulcanized rubber having the same composition as that of the tread rubber of the tire to be evaluated is made as a test specimen, and then the vulcanized rubber is subjected to abrasion by the use of an indoor wear testing machine such as Lambourn abrasion tester.

In this method, there is a possibility that, due to difference in the vulcanizing conditions, characteristics of the vulcanized rubber subjected to the abrasion test differ from those of the tread rubber of the tire to be evaluated. Therefore, there have been a problem such that the estimated result differs from the actual wear resistance.

SUMMARY OF THE INVENTION

It is therefore, an object of the present invention to provide a method for estimating wear resistance of the tread portion of a tire in which a rubber seat cut out from the tread portion of the tire is used as the rubber subjected to an abrasion test, and thereby estimation results having high correlations with actual wear resistance of the tire can be obtained.

According to the present invention, a method for estimating wear resistance of a tread portion of a tire comprises:

a tire manufacturing step in which the tire to be evaluated is manufactured, a rubber seat sampling step in which an evaluation rubber seat is cut out from the tread portion of the tire to include a part of the tread surface, an abrasion step in which the rubber seat is subjected to abrasion by the use of an indoor wear testing machine, and a wear resistance estimating step in which the wear resistance of the tire is estimated based on a state of the wear of the rubber seat caused in the abrasion step.

The thickness of the rubber seat is preferably 0.5 to 4 mm. The indoor wear testing machine preferably comprises a grinding surface rotatable within a plane around an axis perpendicular to this plane, and a roller supported rotatably around an axis parallel with the plane, wherein
the rubber seat is disposed on the outer circumferential surface of the roller, and
in the abrasion step, the rubber seat is placed in contact with the rotating grinding surface.

The indoor wear testing machine preferably comprises a temperature control device for changing the temperature of the grinding surface.

It is preferable that, in the abrasion step, when estimating the wear resistance of the tire rolling on a road surface having any temperature X, the temperature Y of the grinding surface is set in a range of from 1.5 to 3.0 times the temperature X of the road surface.

It is preferable that, in the abrasion step, when estimating the wear resistance of the tire rolling on a road surface whose temperature X1 is not more than 10 deg. C., the temperature control device controls the temperature Y of the grinding surface at a value in a range of from 1.0 to 5.0 times the temperature X1 of the road surface.

It is preferable that, in the abrasion step, when estimating the wear resistance of the tire rolling on a road surface whose temperature X2 is more than 10 deg. C., the temperature control device controls the temperature Y of the grinding surface at a value in a range of from 1.5 to 3.0 times the temperature X2 of the road surface.

DESCRIPTION OF THE PREFERRED EMBODIMENTS

Embodiments of the present invention will now be described in detail in conjunction with the accompanying drawings.

According to the present invention, a method for estimating wear resistance of the tread portion of a tire is an indoor estimating method and comprises a tire manufacturing step K1 in which the tire to be evaluated is manufactured, a rubber seat sampling step K2 in which an evaluation rubber seat is cut out from the tread portion of the tire, an abrasion step K3 in which the rubber seat is subjected to abrasion, and a wear resistance estimating step K4 in which the wear resistance is estimated based on the state of the wear of the rubber seat caused during the abrasion step K3.

In the tire manufacturing step K1, the tire 1 can be manufactured by a known manufacturing method using a vulcanization mold for example. The type of the tire 1 is not limited. Various pneumatic tire for passenger cars, trucks, motorcycles and the like are covered.

Figure 1:
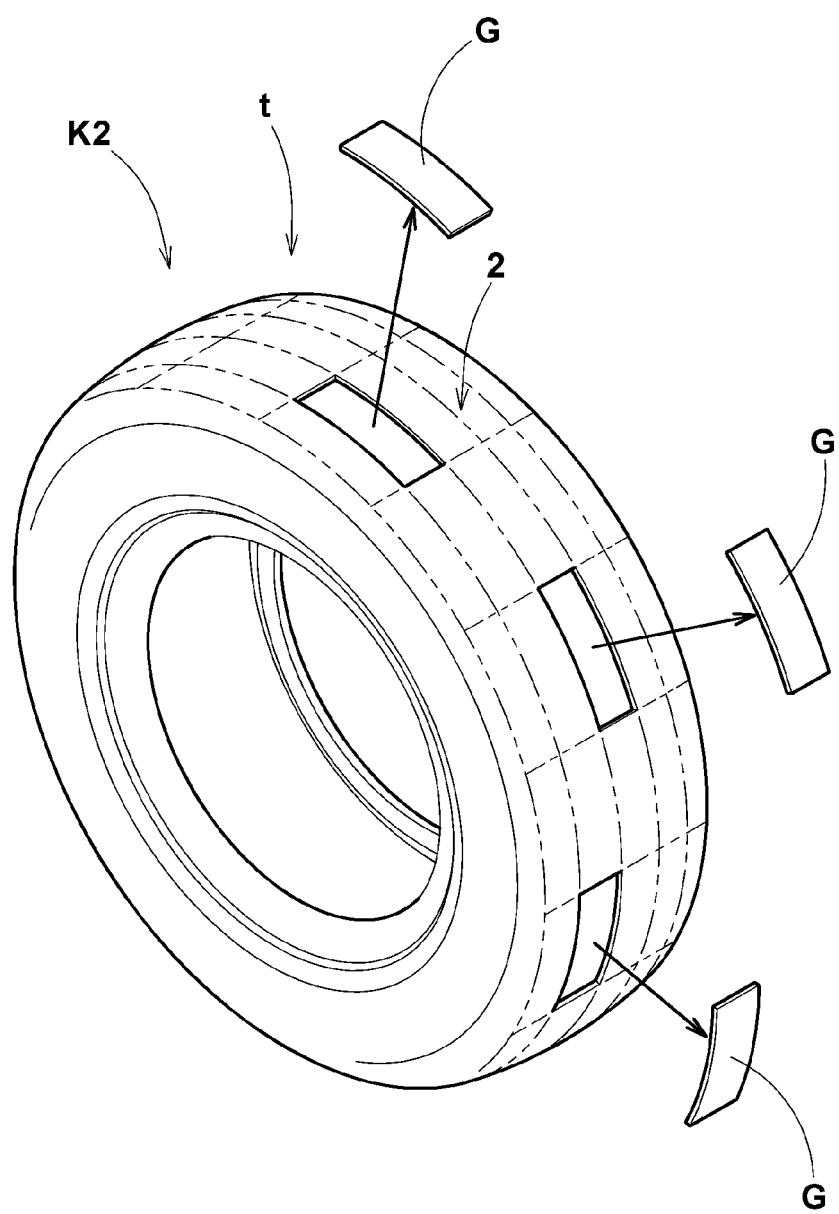
FIG. 1 is a diagram for explaining the seat sampling step.

In the rubber seat sampling step K2, as shown in FIG. 1, an evaluation rubber seat G is cut out from the tread portion 2 of the tire 1 by means of a machine work, a cutting tool such as knife or the like so that the evaluation rubber seat G includes a part of the tread surface. Preferably, the shape of the cut-out rubber seat G is a rectangle.

In the abrasion step K3, various indoor wear testing machines M including known types of machines can be used as far as it is possible to carry out the abrasion test for the vulcanized rubber which is standardized in the Japanese Industrial Standards K6263.

The indoor wear testing machine M used in this embodiment is an improved one based on a rubber wear tester (Type: LAT100) manufactured by Heisen Yoko co. Ltd.

Figure 2:
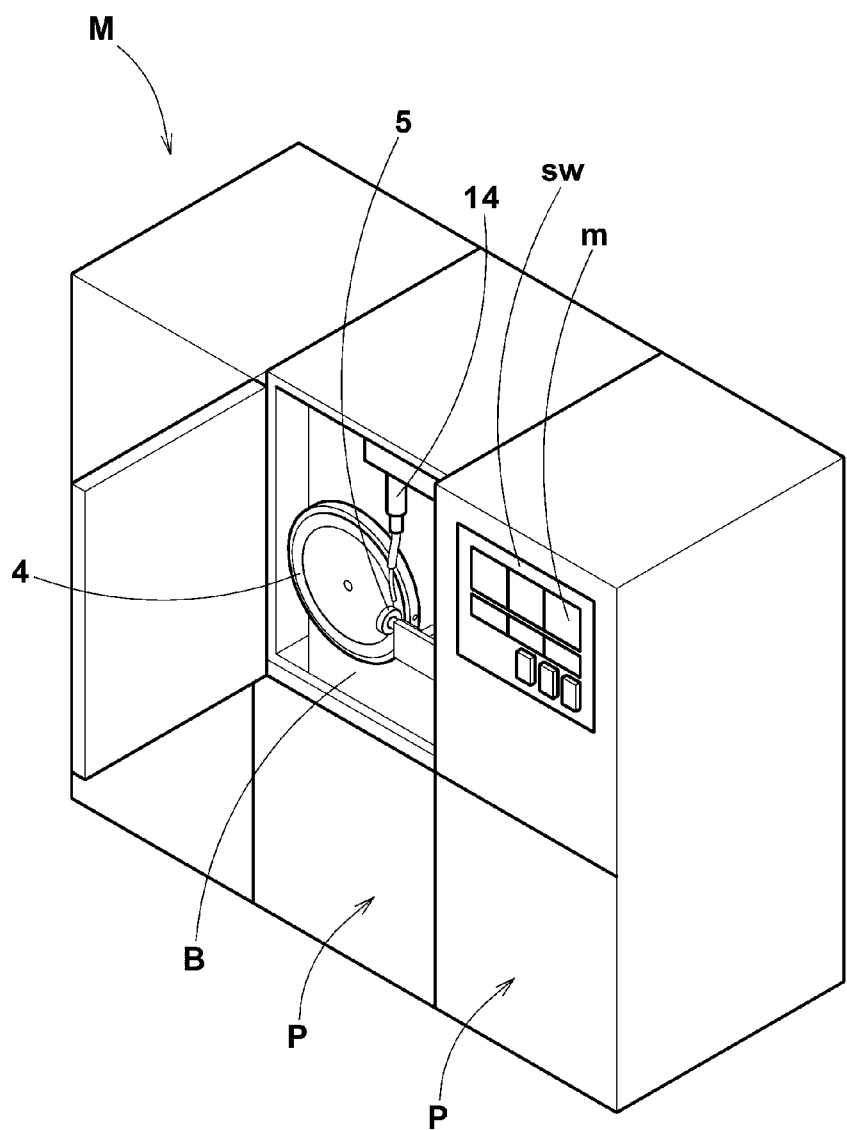
FIG. 2 is a schematic perspective view of an indoor wear testing machine used in the present invention.
Figure 3:
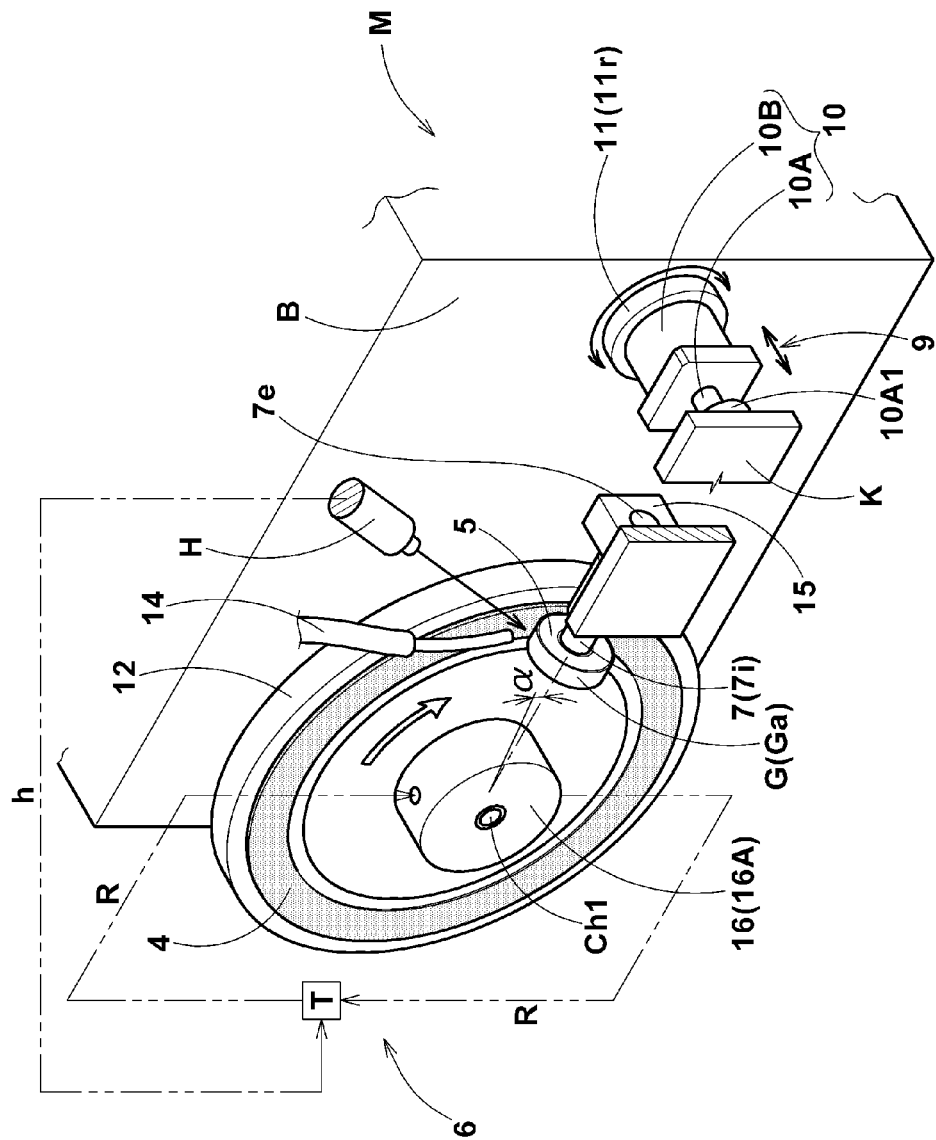
FIG. 3 is a schematic perspective view showing a grinding surface of the indoor wear testing machine shown in FIG. 2.

The indoor wear testing machine M is as shown in FIG. 2 and FIG. 3, shaped in a rectangular parallelepiped.
In the front panel p, there are provided with switches (sw) to control the indoor wear testing machine M, indicators (m) indicating operating conditions and the like.

As shown in FIG. 3, the indoor wear testing machine M in this embodiment is provided on the front of a vertical base frame B with
a grinding surface 4 rotatable within a vertical plane around an axis ch1 perpendicular to the vertical plane,
a roller 5 supported rotatably around an axis 7 parallel with the vertical plane, and a temperature control device 6 for changing the temperature of the grinding surface 4.

Incidentally, it is also possible to construct the indoor wear testing machine M such that the grinding surface 4 is rotatable within a horizontal plane.

The grinding surface 4 in this example is formed on a rotary disk 12 fixed to the above-mentioned axis ch1, and the grinding surface 4 has a shape like a circular ring having a constant width.

The axis ch1 is coupled with an electrical motor (not shown) disposed on the back side of the base B for example. Accordingly, by actuating the electrical motor, the rotary disk 12 and grinding surface 4 are rotated around the axis ch1.

The rubber seat G is firmly applied to the outer circumferential surface 5*a* of the roller 5 by the used of an adhesive agent for example.

In order to continuously subject the rubber seat G to abrasion, the roller 5 with the rubber seat G applied on the outer circumferential surface 5 thereof is pressed against the rotating grinding surface 4.

It is preferred that the abrasive grain on the grinding surface 4 has a grain size in a range of from about 40 to 80 (mesh) in order to obtain high correlativity with the actual wear resistance of the tire rolling on the road.

Figure 4:
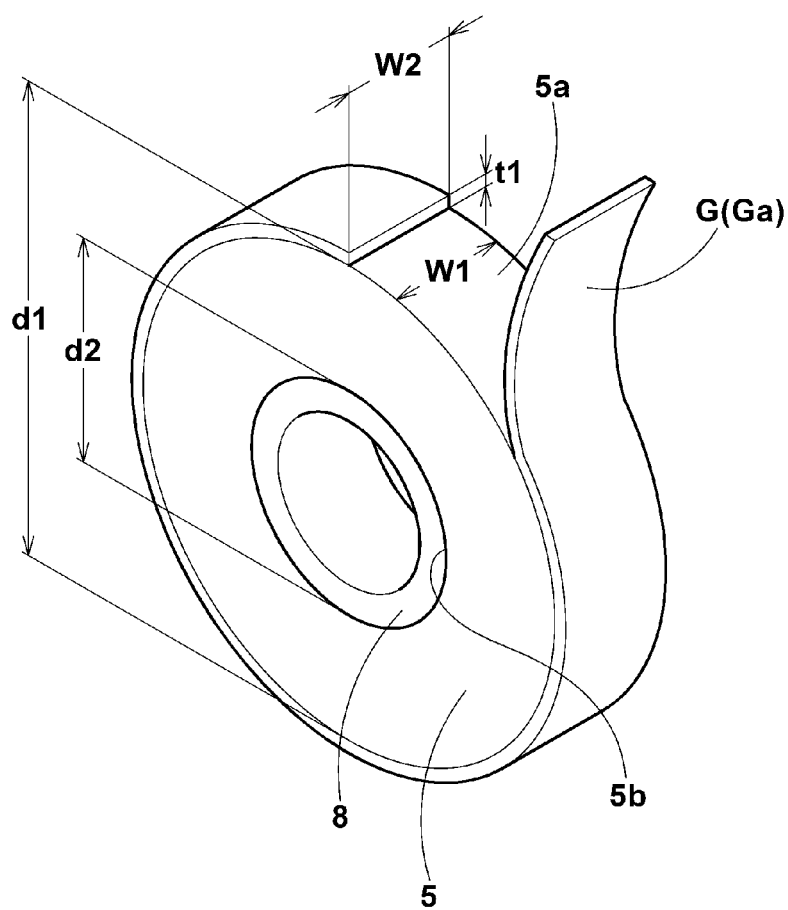
FIG. 4 is a schematic perspective view for explaining a roller.

The roller 5 is as shown in FIG. 4, a tubular body having a through-hole 5*b* at the center thereof. The roller 5 is attached to one end 7*i* of the axis 7 by the use of a bearing 8 disposed in the through-hole 5*b* so that the roller 5 is freely rotatable around the axis 7. Preferably, the roller 5 is made of a rubber material to increase the adhesive force between the rubber seat G and the roller 5.

Preferred dimensions of the roller 5 are for example as follows:

the outside diameter d1 is about 70 to 80 mm, the inside diameter d2 is about 25 to 35 mm, and the width w1 is about 15 to 22 mm.

The thickness t1 of the rubber seat G is preferably set in a range of not less than 0.5 mm, more preferably not less than 1.0 mm, but not more than 4.0 mm, more preferably not more than 3.0 mm.

The width w2 of the rubber seat G is preferably 15 to 22 mm. In this example, the width w2 is the same as the width w1 of the roller 5.

If the thickness t1 is less than 0.5 mm, there is a possibility that the entire thickness of the rubber seat G is worn away during the abrasion test. If the thickness t1 is more than 4.0 mm, it becomes difficult to apply the rubber seat G firmly to the outer circumferential surface 5*a* of the roller 5.

As shown in FIG. 3, the indoor wear testing machine M comprises a roller moving device 9 for moving the roller 5. The roller moving device 9 comprises a cylinder actuator 10 for moving the roller 5 perpendicularly to the grinding surface 4 and a rotation mechanism 11 for moving the roller 5 parallel with the grinding surface 4.

The cylinder actuator 10 comprises a rod 10A making telescopic motions in the longitudinal direction, and a casing 10B supporting the rod 10A. The cylinder actuator 10 is oriented so that the longitudinal direction becomes perpendicular to the grinding surface 4. In this embodiment, one end 10A1 of the rod 10A is connected to the other end 7*e* of the axis 7 through a platy fixing member K for example. As a result, by the telescopic motions of the rod 10A, the cylinder actuator 10 can move the roller 5 so as to contact with or separate from the grinding surface 4.

The other end 7*e* of the axis 7 in this embodiment is provided with an attaching piece 15 which has a rectangular parallelepiped shape and facilitates the fixing to the fixing member K.

In order to give a slip angle α to the roller 5, the rotation mechanism 11 comprises a bearing 11*r* for supporting the cylinder actuator 10 rotatably around an axis perpendicular to the grinding surface 4, and a stopper (not shown) for keeping the rotated state of the bearing 11*r*. The bearing 11*r* is fixed to the base B.

In the contact portion between the grinding surface 4 and the roller 5, a tangential direction to the circumference of the roller 5 and a tangential direction to the circumference of the grinding surface 4 can be differed from each other by rotating the cylinder actuator 10. The angle between the two tangential directions is the slip angle α.

By giving a slip angle α of more than zero to the roller 5, the frictional force between the grinding surface 4 and rubber seat G is increased, and thereby it is possible to efficiently wear the rubber seat G for a short time.

The above-mentioned temperature control device 6 comprises a heat transfer device 16 for heating/cooling the grinding surface 4 on the rotary disk 12, and a heat/cold source T for heating/cooling the heat transfer device 16. The heat/cold source T in this example is of a heat pump type using a medium R.

The heat transfer device 16 comprises a cylindrical front portion 16A disposed on the front side of the grinding surface 4 and around the axis ch1, and a rear portion (not shown) connected to the front portion 16A and disposed on the back side of the rotary disk 12. The heat transfer device 16 has a hollow (not shown) therein.

The front portion 16A in this embodiment is provided with an inlet into which the medium R supplied from the heat/cold source T is injected, and an outlet from which the medium R returning to the heat/cold source T is discharged. The inlet and outlet are formed in the outer circumferential surface 16A1 of the front portion 16A (in FIG. 3, on the upper side and lower side thereof, respectively).

The medium R injected in the heat transfer device 16 through the inlet flows through the hollow so as to heat/cool the entirety of the heat transfer device 16 and then discharged from the outlet. Thereby, the grinding surface 4 is heated/cooled. More specifically, the heat transfer device 16 heats/cools the rotary disk 12, and the grinding surface 4 is heated/cooled by the rotary disk 12. Thus, it is preferable that the heat transfer device 16 is made of a thermally-conductive metal material. Between the rotary disk 12 and a surface behind this, there is a small gap (not shown) not to hinder the rotation of the rotary disk 12.

As to the medium R, for example chlorofluorocarbon may be used. But, oil having a larger specific heat is used in this embodiment.

Further, the indoor wear testing machine M includes a temperature sensor H for measuring the temperature of the grinding surface 4. Various types of sensors may be employed as the temperature sensor H. For example, a noncontact type surface thermometer utilizing visible-light laser is preferably employed. The temperature sensor H outputs a signal h indicating the temperature of the grinding surface 4 which is transmitted to a controller of the heat/cold source T to adjust the temperature of the medium R.

The indoor wear testing machine M is provided with a sand blaster (its entirety is not shown). The sand blaster comprises a blaster nozzle 14 for injecting abrasive between the rubber seat G and the grinding surface 4 to prevent the shavings or dust formed by wearing of the rubber seat G and grinding surface 4 from adhering to the rubber seat G. As to the abrasive, preferably used is for example, a mixture of granular magnesium oxide and granular aluminum oxide.

In the abrasion step K3, the rod 10A of the cylinder actuator 10 is retracted so that the rubber seat G applied to the outer circumferential surface 5a of the roller 5 comes into contact with the grinding surface 4. Then, the grinding surface 4 is rotated and thereby the roller 5 rotates while producing friction against the grinding surface 4 to cause wear of the rubber seat G. At this time, a certain slip angle α is preferably given to the roller 5.

The average rotational speed of the grinding surface 4 is preferably in a range of about 15 to 25 km/h so that the rubber seat G wears orderly.

In this abrasion step K3, the temperature of the grinding surface 4 can be kept at a constant value by the above-mentioned temperature control device 6 according to the output signal h of the temperature sensor H.

Preferably, the temperature control device 6 is constructed such that, when estimating the wear resistance of the tire rolling on a road surface having any temperature X, the temperature control device 6 adjusts the temperature Y of the grinding surface depending on the temperature X of the road surface.

More specifically, when estimating the wear resistance of the tire under a low road surface temperature X1 of not more than 10 deg. C., especially 5 to 10 deg. C., it is preferable that the temperature Y of the grinding surface 4 is set in a range of from 1.0 to 5.0 times the temperature X1.

However, when estimating the wear resistance of the tire under a high road surface temperature X2 of more than 10 deg. C., especially 10 to 50 deg. C., it is preferable that the temperature Y of the grinding surface 4 is set in a range of from 1.5 to 3.0 times the temperature X2.

Therefore, with respect to any temperature X of the road surface, it is possible to set the temperature Y of the grinding surface in a range of from 1.5 to 3.0 times the temperature X.

In the wear resistance estimating step K4, the actual wear resistance of the tire when rolling on the road whose surface temperature is X can be estimated or evaluated based on the state of the wear of the rubber seat G caused in the abrasion step K3 carried out under the temperature Y of the grinding surface 4. More specifically, the wear mass or the mass worn away is obtained by measuring the mass of the rubber seat G before and after the abrasion test and finding the difference therebetween. Then, the obtained wear mass is evaluated by comparing to another example or control.

Confirmation Tests

In order to confirm the correlativity between the temperature of the grinding surface 4 and the temperature of the road surface, the following indoor test and road test were carried out.

The indoor test was carried out according to JIS K6263 under the grinding surface temperature conditions shown in Table 1 by the use of the above-mentioned indoor wear testing machine M.

The rubber seat G (t1=2.0 mm, w2=18 mm) was bonded around the roller 5 (d1=74 mm, d2=30 mm, w1=18 mm).

The roller was pressed onto the grinding surface 4 by a load of 40 N, and rotated at a slip angle of 6 degrees for 6000 meters. Every 1000 meters, the mass of the rubber seat was measured (totally six times) to obtain the wear mass.

The road test was carried out under the road surface temperature conditions shown in Table 1 (average temperature), wherein a Japanese 2000 cc FF passenger car provided on all of the four wheels with the test tires was run for 6000 kilometers on a dry asphalt road of a tire test course.

tire size: 195/65R15 (rim size: 15×6)
tire pressure: 230 kPa
tire load: 4.21 kN
speed: 60 km/h Every 1000 kilometers, the depth of the tread groove was measured (totally six times) to obtain the amount of wear of the tread rubber. More specifically, in each time, the measurement was made at six fixed circumferential positions, and the average value of the measurements was computed as the amount of wear at each time.

For each combination of the road surface temperature and the grinding surface temperature shown in Table 1, the six test results of the indoor test (wear mass) and the six test results of the road test (amount of wear) were plotted on a graph (ordinate: wear mass, abscissas: amount of wear) and the correlation factor R2 was computed.

The correlation factor R2 of 0.8 or higher is considered as being good.

The test results are shown in Table 1.

TABLE 1

| Example No. | 1 | 2 | 3 | 4 | 5 | 6 | 7 | 8 | 9 | 10 |
|---|---|---|---|---|---|---|---|---|---|---|
| grinding surface temp. Y (deg. C.) | −15 | −10 | −5 | 5 | 10 | 15 | 20 | 25 | 30 | −25 |
| road surface temp. X1 (deg. C.) | 5 | 5 | 5 | 5 | 5 | 5 | 5 | 5 | 5 | 10 |
| ratio Y/X1 | −3.0 | −2.0 | −1.0 | 1.0 | 2.0 | 3.0 | 4.0 | 5.0 | 6.0 | −2.5 |
| correlation factor R2 | 0.75 | 0.85 | 0.89 | 0.92 | 0.99 | 0.92 | 0.90 | 0.88 | 0.70 | 0.70 |

| Example No. | 11 | 12 | 13 | 14 | 15 | 16 | 17 | 18 | 19 | 20 |
|---|---|---|---|---|---|---|---|---|---|---|
| grinding surface temp. Y (deg. C.) | −20 | −10 | −5 | 5 | 10 | 20 | 30 | 40 | 50 | 55 |
| road surface temp. X1 (deg. C.) | 10 | 10 | 10 | 10 | 10 | 10 | 10 | 10 | 10 | 10 |
| ratio Y/X1 | −2.0 | −1.0 | −0.5 | 0.5 | 1.0 | 2.0 | 3.0 | 4.0 | 5.0 | 5.5 |
| correlation factor R2 | 0.82 | 0.84 | 0.70 | 0.70 | 0.99 | 0.90 | 0.88 | 0.85 | 0.80 | 0.70 |

| Example No. | 21 | 22 | 23 | 24 | 25 | 26 | 27 | 28 | 29 | 30 |
|---|---|---|---|---|---|---|---|---|---|---|
| grinding surface temp. Y (deg. C.) | −15 | 15 | 23 | 30 | 45 | 50 | 25 | 40 | 50 | 75 |
| road surface temp. X2 (deg. C.) | 15 | 15 | 15 | 15 | 15 | 15 | 25 | 25 | 25 | 25 |
| ratio Y/X2 | −1.0 | 1.0 | 1.5 | 2.0 | 3.0 | 3.3 | 1.0 | 1.6 | 2.0 | 3.0 |
| correlation factor R2 | 0.60 | 0.70 | 0.81 | 0.95 | 0.90 | 0.70 | 0.75 | 0.81 | 0.99 | 0.90 |

| Example No. | 31 | 32 | 33 | 34 | 35 | 36 | 37 | 38 | 39 | 40 |
|---|---|---|---|---|---|---|---|---|---|---|
| grinding surface temp. Y (deg. C.) | 80 | 35 | 55 | 70 | 80 | 45 | 70 | 80 | 50 | 80 |
| road surface temp. X2 (deg. C.) | 25 | 35 | 35 | 35 | 35 | 45 | 45 | 45 | 50 | 50 |

TABLE 1-continued

| ratio Y/X2 | 3.2 | 1.0 | 1.6 | 2.0 | 2.3 | 1.0 | 1.6 | 1.8 | 1.0 | 1.6 |
|---|---|---|---|---|---|---|---|---|---|---|
| correlation factor R2 | 0.70 | 0.71 | 0.88 | 0.95 | 0.92 | 0.75 | 0.85 | 0.95 | 0.70 | 0.90 |

As shown in Table 1, when the temperature X2 of the road surface is more than 10 deg. C., by setting the temperature Y of the grinding surface 4 in a range of from 1.5 to 3.0 times the temperature X2, the correlation factor R2 becomes very good.

Further, when the temperature X1 of the road surface is not more than 10 deg. C., the correlation factor R2 becomes very good by setting the temperature Y of the grinding surface 4 in a range of from 1.0 to 5.0 times the temperature X1.

In the test results shown in Table 1, when the low road surface temperature X1 was 5 to 10 deg. C., the correlation factor R2 also became good by setting the temperature Y of the grinding surface 4 in a range of from −2.0 to −1.0 times the temperature X1.

As described above, in the estimating method according to the present invention, since a rubber seat cut out from the tread portion of the tire is used, estimation results having high correlations with the actual wear resistance can be obtained.

The invention claimed is:

1. A method for estimating wear resistance of a tread portion of a tire comprising:

a tire manufacturing step in which the tire to be evaluated is manufactured;

a rubber seat sampling step in which a rubber seat to be evaluated is cut out from the tread portion of the tire including a part of the tread surface;

an abrasion step in which the rubber seat is subjected to abrasion by the use of an indoor wear testing machine, the indoor wear testing machine comprising a grinding surface rotatable within a plane around an axis perpendicular to said plane, and a roller supported rotatably around an axis parallel with the plane, wherein the rubber seat is disposed on the outer circumferential surface of the roller and placed in contact with the rotating grinding surface; and a wear resistance estimating step in which the wear resistance of the tire is estimated based on a state of the wear of the rubber seat caused in the abrasion step, wherein if estimating the wear resistance of the tire rolling on a road surface having a temperature X, the abrasion step comprises controlling the temperature Y of the grinding surface at a value in a range of from 1.5 to 3.0 times the temperature X of the road surface.

2. The method according to claim 1, wherein the thickness of the rubber seat is 0.5 to 4 mm.

3. The method according to claim 1, wherein the indoor wear testing machine has a temperature control device for changing the temperature of the grinding surface.

4. A method for estimating wear resistance of a tread portion of a tire comprising:

a tire manufacturing step in which the tire to be evaluated is manufactured;

a rubber seat sampling step in which a rubber seat to be evaluated is cut out from the tread portion of the tire to include a part of the tread surface;

an abrasion step in which the rubber seat is subjected to abrasion by the use of an indoor wear testing machine, the indoor wear testing machine comprising a grinding surface rotatable within a plane around an axis perpendicular to said plane, and a roller supported rotatably around an axis parallel with the plane, wherein the rubber seat is disposed on the outer circumferential surface of the roller and placed in contact with the rotating grinding surface; and a wear resistance estimating step in which the wear resistance of the tire is estimated based on a state of the wear of the rubber seat caused in the abrasion step, wherein if estimating the wear resistance of the tire rolling on a road surface having a temperature X1 not more than 10° C., the abrasion step comprises controlling the temperature Y of the grinding surface at a value in a range of from 1.0 to 5.0 times the temperature X1 of the road surface, and if estimating the wear resistance of the tire rolling on a road surface having a temperature X2 more than 10° C., the abrasion step comprises controlling the temperature Y of the grinding surface at a value in a range of from 1.5 to 3.0 times the temperature X2 of the road surface.

* * * * *